(12) United States Patent
Haar

(10) Patent No.: US 7,985,057 B2
(45) Date of Patent: Jul. 26, 2011

(54) MICROPUMP FOR PERISTALTIC PUMPING OF A LIQUID MEDIUM

(75) Inventor: Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1168 days.

(21) Appl. No.: 11/686,176

(22) Filed: Mar. 14, 2007

(65) Prior Publication Data

US 2008/0038128 A1    Feb. 14, 2008

(30) Foreign Application Priority Data

Mar. 14, 2006   (EP) ..................................... 06111091

(51) Int. Cl.
*F04B 43/12*        (2006.01)
(52) U.S. Cl. ........................ 417/479; 417/474
(58) Field of Classification Search ............... 417/474, 417/475, 476, 479, 63; 604/153; 73/149, 73/290 R
See application file for complete search history.

(56) References Cited

U.S. PATENT DOCUMENTS

| | | | |
|---|---|---|---|
| 5,049,047 | A | 9/1991 | Polaschegg et al. |
| 5,205,819 | A | 4/1993 | Ross et al. |
| 5,478,211 | A | 12/1995 | Dominiak et al. |
| 6,349,740 | B1 | 2/2002 | Cho et al. |
| 6,416,294 | B1 | 7/2002 | Zengerle et al. |
| 6,692,241 | B2 * | 2/2004 | Watanabe et al. .......... 417/477.2 |
| 6,878,132 | B2 | 4/2005 | Kipfer |
| 7,066,909 | B1 | 6/2006 | Peter et al. |
| 2002/0071785 | A1 | 6/2002 | Beach et al. |
| 2004/0204673 | A1 | 10/2004 | Flaherty |
| 2005/0075624 | A1 | 4/2005 | Miesel |
| 2005/0123420 | A1 | 6/2005 | Richter et al. |

FOREIGN PATENT DOCUMENTS

| | | |
|---|---|---|
| EP | 0949418 B1 | 1/2004 |
| WO | 98/47552 A1 | 10/1998 |
| WO | 01/24854 A1 | 4/2001 |

* cited by examiner

*Primary Examiner* — William H Rodríguez
*Assistant Examiner* — Philip Stimpert
(74) *Attorney, Agent, or Firm* — Kristina E. Swanson; Roche Diagnostics Operations, Inc.

(57) ABSTRACT

The invention relates to a micropump for peristaltic pumping of a liquid medium and to a device which contains a peristaltic micropump and which is for metered administration of a liquid drug.

4 Claims, 5 Drawing Sheets

MICROPUMP FOR PERISTALTIC PUMPING OF A LIQUID MEDIUM

REFERENCE TO RELATED APPLICATIONS

The present application claims priority to European Patent Application No. 06111091.2, filed Mar. 14, 2006, which is hereby incorporated by reference in its entirety.

TECHNICAL FIELD

The invention relates to a micropump for peristaltic pumping of a liquid medium and to a device which contains a peristaltic micropump and which is for metered administration of a liquid drug.

BACKGROUND

Among the devices used for the administration of liquid drugs are portable infusion devices. These infusion devices replace injection with a syringe or with an injection pen.

An example of such an infusion device is an insulin pump for the administration of insulin, such pumps being used in particular by diabetics who are treated with intensified insulin therapy and who measure their blood glucose levels regularly. The insulin pump is carried outside the patient's body, on the belt for example. By means of a thin tube (infusion set or catheter), the cannula of which sits under the patient's skin, the infusion pump delivers a continuous supply of insulin to the body to meet the patient's basal insulin requirement. Additional insulin, such as that required at mealtimes for example, can be supplied by the patient pressing a button.

Infusion devices known from the prior art contain a pump whereby the liquid drug to be administered is pumped from the infusion device. Normally, the infusion device contains a container as a liquid-drug reservoir, from which the drug is displaced by means of a plunger and administered.

Metered dosing of minute quantities of liquid at the microlitre or nanolitre level is becoming increasingly important in many areas of application, e.g. analysis or environmental engineering, as well as medical technology. Pump arrangements that automatically monitor whether the desired quantity of liquid has actually been delivered must therefore be found. Discrepancies between the quantity delivered and the quantity desired can, for example, be caused by a malfunction of the pump or a blockage of the pump passages.

SUMMARY

The object of this invention is therefore to avoid the disadvantages of the prior art and, in particular, to enable the quantity of liquid delivered by a micropump to be monitored. A further object of this invention is to provide a peristaltic micropump which operates more reliably.

According to one aspect of the invention, a micropump for peristaltic pumping of a liquid medium has at least one flow channel with a wall element, the flow channel having a cross-sectional area which, at least in subportions of the flow channel, can be altered by the exertion of a force on the wall element of the flow channel, and at least one actuator which is arranged in such a manner that it is able to exert a force on the wall element of the flow channel in a portion of the channel to reduce the cross-sectional area in the portion of the channel.

The micropump also includes at least one sensor arrangement for detecting a quantity of liquid medium in the portion of the channel, the sensor arrangement being located outside the flow channel.

The pump according to the invention has at least one flow channel with a wall element. The wall element is, for example, a tube, in particular an infusion tube, or it has at least one membrane area. The cross-sectional area of the flow channel can be altered, at least in subportions of the flow channel, by the exertion of a force on the wall element. The wall element is preferably made of an elastic material, at least in these subportions. The pump according to the invention also has at least one actuator which can exert a force on the wall element in a portion of the flow channel and thereby reduce the cross-sectional area in the portion of the channel. A liquid medium contained in this portion of the channel can thus be at least partially displaced from the portion of the channel. Depending on design of the wall element, the flow channel, and the actuators, small quantities of liquid medium—in particular, down to 10 mL/min—can be pumped with the micropump according to the invention. This is made possible in particular by the fact that in the micropump according to the invention, unlike in the described infusion pumps with a displacing plunger in the liquid-medium reservoir, small volumes are pumped out of small volumes.

The peristaltic micropump in this invention also has a sensor arrangement for detecting a quantity of liquid medium in the portion of the channel, and the cross-sectional area of the portion of the channel can be altered by the exertion of a force. This sensor arrangement lies outside the flow channel. It therefore detects the quantity of liquid medium in the portion of the channel without being in direct contact with the liquid medium.

Another aspect of the invention relates to a method for monitoring a micropump for peristaltic pumping of a liquid medium. The micropump has at least one flow channel with a wall element, the flow channel having a cross-section area which, at least in subportions of the flow channel, can be altered by the exertion of a force on the wall element of the flow channel, and comprises at least one actuator which is arranged in such a manner that it is able to exert a force on the wall element of the flow channel in a portion of the channel to reduce the cross-sectional area in the portion of tile channel.

In the method according to the invention, at least one sensor arrangement located outside the flow channel detects a quantity of liquid medium in the portion of the channel. The sensor arrangement in this invention detects a measurement signal (e.g. absorbance, fluorescence, capacity) whereby it is for example possible, with knowledge of other parameters (e.g. the flow-channel diameter, the length of the portion of the channel, properties of the liquid medium), to calculate a volume of the liquid medium in the portion of the channel.

By measuring the quantity of liquid medium with the sensor arrangement in the micropump according to the invention and with the method according to the invention, it is possible to ensure that the pump delivers the intended quantity of liquid medium or that a delivery error is detected. If several sensor arrangements are provided, the quantity of liquid medium can even be measured and tracked in individual areas of the pump. Monitoring to check that the micropump is working as desired and actually delivering the right quantity of liquid medium is thus guaranteed, irrespective of the pump mechanism. Such monitoring is important particularly for infusion pumps for liquid drugs, e.g. for insulin pumps, as administration of the wrong dosage can result in health damage.

In a preferred embodiment of this invention, the micropump has at least two actuators which are arranged in such a way that they are able to exert a force on the wall element of the flow channel in at least two portions of the channel, thereby temporarily closing the relevant portion of the channel and allowing a volume segment to be isolated in the flow channel, the quantity of liquid medium in the volume segment being detected by means of a sensor arrangement which lies outside the wall element of the flow channel. In the method according to the invention, at least two actuators temporarily close two portions of the channel, thereby isolating, between the two closable portions of the channel, a volume segment, which may contain liquid medium that is to be pumped on further. The quantity of liquid medium in the volume segment is detected by means of a sensor arrangement which lies outside the flow channel.

A first variant of this embodiment is, for example, a micropump with several cylindrical actuators which are arranged on a circular circumference about a rotating shaft (in a rotary pump), the flow channel running in a curved course in an area along the circular circumference. Two cylindrical actuators at a time can temporarily close the flow channel in the channel portions to which they are currently adjacent, by the exertion of a force from outside. The way in which this is done is that the cylindrical actuators compress the wall element at the site at which they are positioned at the time, thereby reducing the cross-sectional area of the flow channel to virtually zero in the relevant portion of the channel. In the flow channel, between each two channel portions closed by the force of the cylindrical actuators, there is a volume segment, which can contain liquid medium or air for example. When the shaft of the pump rotates, the cylindrical actuators move along the curved flow channel, with the result that the channel portions closed by the actuators, and thus also the volume segment in the channel portion lying between them, likewise move along the flow channel. Outside the flow channel there is at least one sensor arrangement which, in a volume segment that can be detected by the sensor arrangement, detects the quantity of liquid drug in the volume segment.

This first variant therefore represents a micropump which is a rotary pump with cylindrical actuators, the cylindrical actuators being arranged in a circle around a rotatable shaft, and the flow channel running in a curved course along an area adjacent to the cylindrical actuators. This rotary pump pumps the desired quantity of liquid medium by moving small, defined volume segments by means of the cylindrical actuators, as already described.

A second variant of this embodiment is, for example, a micropump that has three pin-shaped actuators which are arranged next to each other on the wall element of the flow channel. The two outer actuators (valve pins) can temporarily close the flow channel by the exertion of a force, with the result that a volume segment is isolated in the channel portion between the channel portions closed by the two actuators. A sensor arrangement assigned to this middle portion of the channel detects a quantity of liquid medium contained within the volume segment. This quantity can also be zero, for example if the middle actuator (pump pin) likewise closes the middle portion of the channel or if the portion of the channel contains air and no liquid medium.

This second variant therefore represents a micropump that contains at least three pin-shaped actuators which are arranged next to each other on the wall element of the flow channel and which comprise at least two valve pins and at least one pump pin. This pump, which operates according to the peristaltic principle, pumps the desired quantify of liquid medium by specifically opening and dosing the three channel portions that lie next to each other and that are assigned to the three pin-shaped actuators, in a certain sequence, with the result that the desired quantity of liquid medium is conveyed further in a certain direction in the flow channel.

The micropump contains at least two further sensor arrangements for detecting the quantity of liquid medium in the at least two closable portions of the channel, the at least two further sensor arrangements lying outside the flow channel. The two further sensor arrangements lying outside the flow channel detect the quantity of liquid medium in the two channel portions that can be closed by the valve pins. In this way, it is possible to detect what quantity of liquid medium is currently present in the relevant portion of the channel and thus to track the movement of the liquid medium through the portions of the channel.

The actuators of the micropump according to the invention can, for example, comprise a piezo actuator, a bimetallic actuator, or an eccentric on a rotating shaft. A micropump with three pin-shaped actuators arranged on the wall element of the flow channel comprises, for example, three piezo actuators, three bimetallic actuators, or three eccentrics on a rotating shaft. Shape memory alloy-based actuators or magnetic pulse switches with two states can also be used as actuators of the micropump according to the invention. The actuators react to controlled changes in certain parameters such as temperature or electrical potential with defined actuator effects, by means of which a force is specifically exerted on the wall element of the flow channel, or not, to reduce the cross-sectional area of a portion of the channel.

In a further embodiment of this invention, a rotatable disc that rotates about an eccentric axis is employed as the actuator, the flow channel running in a near-circular course in an area adjacent to the rotatable disc or to a further disc that can be operated via the rotatable disc.

The micropump's sensor arrangement comprises an electromagnetic radiation-emitting element which is directed at an at least partially radiotransparent area of the wall element of the flow channel and an electromagnetic radiation-detecting element which is likewise directed at an at least partially radiotransparent area of the wall element of the flow channel and which is arranged in such a way that it can detect electromagnetic radiation which has crossed the flow channel and which emerges from the area of the wall element. The method of measurement used by this sensor arrangement is based on the absorption of the electromagnetic radiation or the generation of fluorescence in the channel portion into which the radiation-emitting element emits electromagnetic radiation. The absorption is determined by measurement of the unabsorbed (transmitted) fraction of the emitted electromagnetic radiation by means of the electromagnetic radiation-detecting element. The fraction absorbed depends on the materials and the path which the radiation follows through the materials in the portion of the channel (as well as on the material and the path which the radiation follows through the wall element). Therefore, if the absorption behaviour of the liquid medium and the possible dimensions of the flow route in the area of the channel portion on which the sensor arrangement is located are known, the quantity of liquid medium in the portion of the channel can be determined from the measured intensity of the transmitted radiation or from the intensity of the fluorescence radiation generated by the emitted electromagnetic radiation.

The emitted electromagnetic radiation is monochromatic and has a wavelength that is appropriate to the absorption properties or, where applicable, a fluorescence wavelength of the liquid medium. The at least one sensor arrangement of the micropump according to the invention comprises, for this purpose, an electromagnetic radiation-emitting element which emits electromagnetic radiation at a wavelength that is preferably in the region of an absorption maximum of the liquid medium or at a fluorescence wavelength of the liquid medium. If the liquid medium contains water for example, an emitted electromagnetic radiation wavelength in the region of the absorption maximum of water at 3 μm can be selected, e.g. a wavelength of between 3 μm and 15 μm. Thus if there is wafer in the channel portion through which the electromagnetic radiation passes, a large fraction of the emitted electromagnetic radiation is absorbed. If the portion of the channel contains air for example, much less is absorbed. If the portion of the channel is closed (cross-sectional area of the flow route virtually zero), virtually no radiation is absorbed, apart from the fraction absorbed by the material of the wall element.

The absorption properties or the fluorescence properties of an excipient added to the liquid medium (possibly for this purpose only), e.g. a preservative, may also be taken into account, however. The concentration of the excipient in the liquid medium must be high enough for the absorption or the fluorescence of the electromagnetic radiation to be detectable. The excipient may, for example, have an absorption maximum in the near UV (e.g. 320 nm), and the electromagnetic radiation-emitting element may emit radiation in the region of this wavelength.

In this invention the material chosen for the wall element is preferably such that if causes as little absorption of the electromagnetic radiation as possible. If the micropump according to the invention is used for metered administration of liquid drugs, the material of the wall element (e.g. the infusion tube) must be biocompatible. For insulin-pump tubes, at least one material selected from the following group: ethylene-vinyl acetate copolymer (EVA), polyvinyl chloride (PVC), polyurethane (PU), and polyethylene (PE) is preferably used in this invention. An external tube and an internal tube made of different materials can be used if necessary.

In one embodiment of this invention, the wall element can have a wall area which is formed so as to be at least partially reflective, and the electromagnetic radiation-detecting element can be arranged in such a way that it can defect radiation which is emitted by the electromagnetic radiation-emitting element and reflected by the wall area. In this arrangement, the ray path of the electromagnetic radiation passes through the flow channel in the channel portion, in which the quantity of liquid medium is to be detected, twice before it is detected by the detecting element.

In a further embodiment of the micropump according to the invention, the electromagnetic radiation-emitting element and the electromagnetic radiation-detecting element are arranged on opposite sides of the flow channel, outside the wall element. In this arrangement, the emitted electromagnetic radiation passes through the flow channel in only one direction before the transmitted fraction is detected.

A laser, for example a laser diode, a light diode, or an illuminating element made of electronic polymers may be used as an electromagnetic radiation-emitting element in this invention. The chosen electromagnetic radiation-emitting element is preferably one that can be advantageously connected, by virtue of its shape, to the wall element of the flow channel (e.g. a tube). A photodiode, a phototransistor, another semiconductor detector, or a simple CMOS multiple detector unit can be used as an electromagnetic radiation-detecting element in this invention. The electromagnetic radiation-detecting element may be integrated into an electronic circuit.

In a further embodiment of this invention, the sensor arrangement comprises a capacitor which contains capacitor plates arranged on two sides of the portion of the flow channel, outside the wall element. The sensor arrangement also comprises a measuring arrangement for measuring the capacitance of the capacitor. With this sensor arrangement, the quantity of liquid medium contained in the portion of the channel can be determined capacitively. The capacitance of the capacitor is measured with a measuring arrangement familiar to a person skilled in the art, e.g. through detuning of a tuned circuit. The capacitance is determined by the composition and quantity of material between the condenser plates. For example, filling a tube running between the capacitor plates with water increases the capacitance of the capacitor on account of water's dielectric constant of approximately 90.

In a further embodiment of this invention, the sensor arrangement comprises an ultrasound sensor containing an ultrasound emitter and an ultrasound receiver which are arranged on two sides of the portion of the flow channel (e.g. next to or opposite each other), outside the wall element. The ultrasound emitter generates an ultrasound signal—e.g. by means of a piezoelectric material—which passes through the wall element into the flow channel. The ultrasound sensor receives an ultrasound signal from the flow channel, the strength of the signal depending, in particular, on the ultrasound energy reflected in the flow channel or transmitted by it. This reflected or transmitted ultrasound energy is determined by the acoustic impedance mismatch of the materials used, in particular the wall element material and the material contained in the portion of the channel. The acoustic impedance mismatch provides the basis for the detection of the quantity of liquid medium contained in the portion of the channel.

Consequently, in the particularly preferred methods according to the invention for monitoring the micropump according to the invention, the at least one sensor arrangement measures the absorption or transmission of electromagnetic radiation, the fluorescence, a reflected or transmitted acoustic signal, or the change in capacitance in a portion of the channel.

The invention also relates to a device for metered administration of a liquid drug, containing a micropump according to the invention, a reservoir of the liquid drug, and an infusion needle arrangement. The reservoir being connected to the infusion needle arrangement by means of the flow channel.

Such a device is, for example, an insulin pump which has a replaceable or refillable reservoir of insulin. The liquid drug is pumped from the reservoir, via the flow channel, to the infusion needle arrangement by the micropump of the device according to the invention and is then administered to a patient, in a metered dose, via an infusion needle. The pumped quantity of liquid drug and the functional adequacy of the micropump are monitored in the process by the sensor arrangement contained in the micropump.

The device according to the invention for metered administration of the liquid drug includes a control unit which controls the micropump. The control unit can be sited right next to the micropump, e.g. in a common housing, or be remote from the micropump. For example, the control unit can be located in a first housing which a patient can attach to a belt, and the micropump can be sited near the infusion needle arrangement. Communication between the control unit and the micropump may be effected wirelessly or via a connecting signal lead.

In the device according to the invention, the micropump can be located in the same housing as the reservoir, in the same housing as the infusion needle, arrangement, or separately, outside the wall element of the flow channel, between the reservoir and the infusion needle arrangement.

Siting the micropump near to the infusion needle arrangement (irrespective of the position of a control unit) has the advantage that the monitoring, by the sensor arrangement, of the quantity of liquid drug pumped by the micropump takes place near to the infusion site and thus that monitoring to see whether the desired quantity is being administered is carried out with a high degree of reliability.

A control unit of the micropump initiates a reaction if the quantity of liquid medium detected in a portion of the channel with the at least one sensor arrangement deviates from an expected quantity by more than a predetermined difference, the reaction being at least one reaction chosen from among the following group: halting of the micropump, issuing of an optical warning signal, issuing of a haptic warning signal, issuing of an acoustic warning signal, and issuing of a signal that is received by a remote receiver resulting in the issuing of a warning signal there.

The optical warning signal can, for example, be a flashing warning light, or a text that describes the problem on a display (possibly on the control unit). The haptic warning signal can, for example, be the vibrating of a portable device carried on the patient's body, possibly the control unit. The acoustic warning signal can, for example, be a warning sound issued by the control unit. The control unit may also send a signal to a remote receiver, where the signal triggers the issuing of an optical, haptic, and/or acoustic warning signal. The remote receiver is, for example, a wrist watch or a mobile phone which may be provided for the purpose of issuing the warning signal for the attention of the patient himself or of another person. Communication between the control unit and the receiver may be effected via a signal lead or wirelessly.

The wall element of the flow channel is detachably mounted in the micropump. The advantage of this is that the wall element (a tube for example) can be provided as a throw-away single-use part that can be disposed of (with the emptied liquid-medium reservoir and/or a used infusion needle arrangement, if necessary) when desired and that the micropump can be reused.

The invention also relates to the use of a micropump according to the invention for pumping insulin or a painkiller, the use of at least one sensor arrangement in a micropump according to the invention for monitoring the quantity of liquid medium pumped, and/or the use of at least one sensor arrangement in a micropump according to the invention for detecting blockages.

A blockage may, for example, be detected when an actuator of the micropump is supposed to close a portion of the flow channel or at least reduce its cross-sectional area at a certain time, but the sensor arrangement located on the portion of the channel detects no, or too small a, reduction in the quantity of liquid medium in the portion of the channel. This indicates a blockage of the flow channel.

The invention is explained in greater detail below with the aid of the drawing.

BRIEF DESCRIPTION Of THE DRAWINGS

The following detailed description of the embodiments of the present invention can be best understood when read in conjunction with the following drawings, where like structure is indicated with like reference numerals and in which.

Figure 1A:
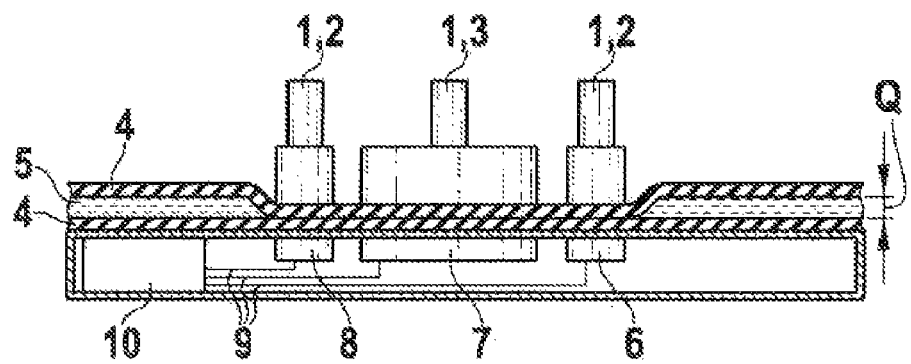
FIGS. 1A to 1D show schematic diagrams of the mode of operation of a micropump according to the invention with pin-shaped actuators.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

DETAILED DESCRIPTION

The following description of the preferred embodiment is merely exemplary in nature and is in no way intended to limit the invention or its application or uses.

FIGS. 1A to 1D show a movement sequence of pin-shaped actuators of a micropump according to the invention.

The micro-pump has three pin-shaped actuators 1, two valve pins 2, and a pump pin 3. The three actuators 1 are arranged next to each other, on the outside of a wait element 4 of a flow channel 5. The wall element 4 is elastic—at least in the area of the three channel portions that are flanked by the actuators—so that the actuators can reduce the cross-sectional area Q of the flow channel 5 by the exertion of a force on the wall element of the relevant portion of the channel. The micropump according to the invention also has three sensor arrangements 6, 7, 8, each of which is assigned to a channel portion beside one of the pin-shaped actuators 1. The sensor arrangements 6, 7, 8 are used for measuring the quantity of liquid medium in the relevant portion of the channel. The sensor arrangements 6, 7, 8 are connected, via signal leads 9, to an evaluation unit 10 for evaluating the signals measured by the relevant sensor arrangement 6, 7, 8.

To pump a volume segment (from right to left in the figure), the micropump according to the invention goes through the movement sequence shown in FIGS. 1A to 1D. In FIG. 1A, all three pin-shaped actuators 1 exert a force on the wall element 4 of the flow channel 5, with the result that the cross-sectional area Q of the flow channel 5 is reduced in all three channel portions assigned to the actuators 1, in such a way that the portions of the channel are closed. The sensor arrangements 6, 7, 8 thus detect no or only a small quantity of liquid medium in the assigned channel portions.

Figure 1B:
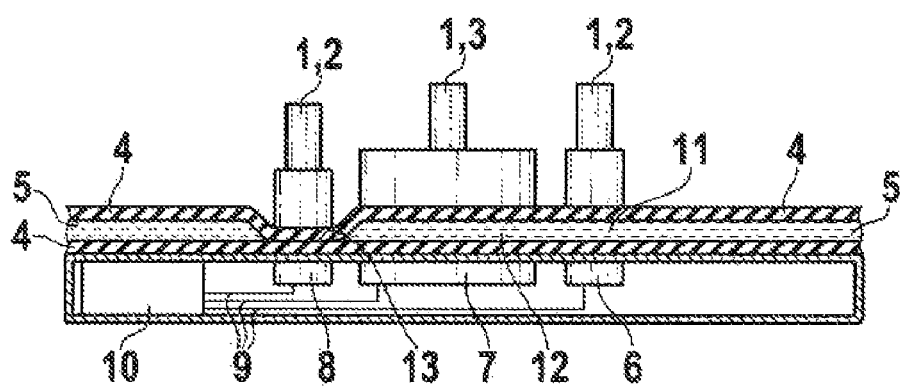

In FIG. 1B, the first valve pin 2 and the pump pin 3 no longer exert any force on the wall element 4, with the result that the flow channel 5 is open in the associated channel portions 11, 12 and has its original cross-sectional area Q. Liquid medium now enters the two channel portions 11, 12. The second valve pin 2 continues to exert a force on the wall element 4 in the third channel portion 13 and closes the flow channel 5 in this portion 13. The first two sensor arrangements 6 and 7 therefore detect the quantify of liquid medium present in the first two channel portions 11, 12; the third sensor arrangement 8 detects no or only a small quantity of liquid medium in the third channel portion 13.

Figure 1C:
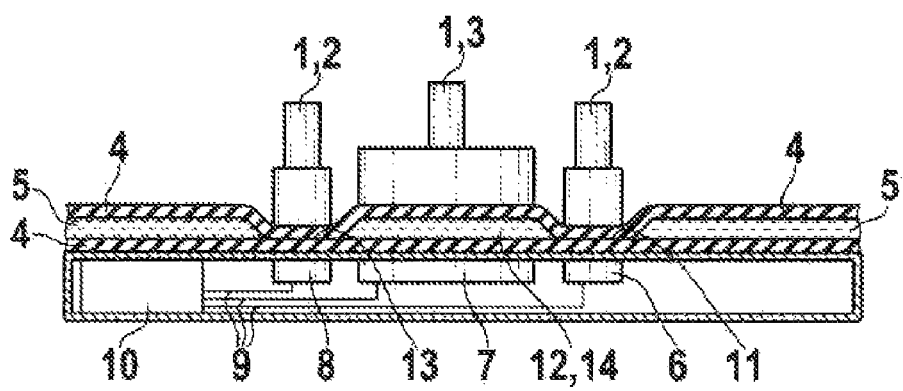

In FIG. 1C, both valve pins 2 exert a force on the wall element 4, with the result that the flow channel 5 is at least largely closed in the first channel portion 11 and the third channel portion 13. The pump pin 3 continues to exert no force on the wall element 4. A volume segment 14 is thus isolated in the second channel portion 12 by the two closed channel portions 11, 13. The second sensor arrangement 7 detects the quantity of liquid medium in the volume segment 14. This quantity depends, among other things, on the dimensions of the second channel portion 12. The tube that is preferably used as the wall element 4 can, for example, have an internal diameter of between 0.1 and 0.3 mm. If the second channel portion 12, and thus the volume segment 14, has a length of between 1 and 3 mm, the volume of the volume segment 14 that is to be pumped by the micropump is approximately 10 to 200 nl. The first and the third sensor arrangements 6, 8 detect no or little liquid medium in the first and third channel portions 11, 13.

Figure 1D:
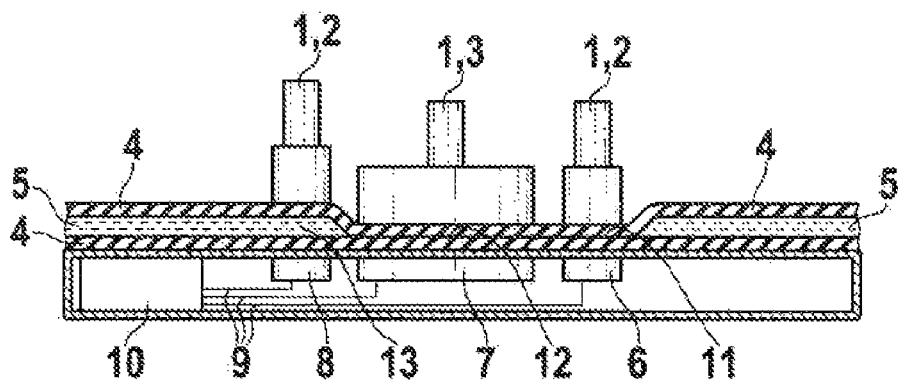

In FIG. 1D, the second valve pin 2 exerts no force on the wall element 4, and the third channel portion 13 is open. The first channel portion 11 remains closed as a result of the action of the first valve pin 2. The pump pin 3 has closed the second channel portion 12 through the exertion of a force on the wall element 4 and thereby displaced the liquid medium (from the volume segment 14) into the third channel portion 13 and the flow channel 5 beyond it. The first and the second sensor arrangements 6, 7 detect no or little liquid medium in the first and second channel portions 11, 12. The third sensor arrangement 8 detects a quantity of liquid medium in the third channel portion 13.

The movement sequence then begins again as shown in FIG. 1A. The liquid medium transported through the three channel portions 11, 12, 13 can be reliably monitored by the three sensor arrangements 6, 7, 8.

Figure 2:
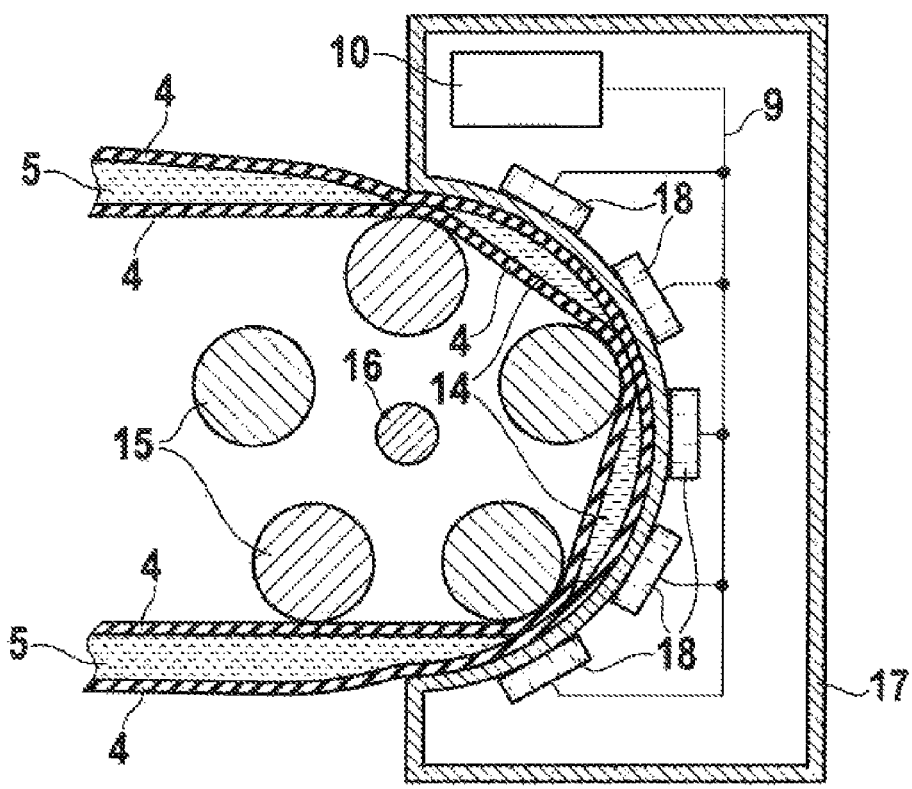
FIG. 2 shows a schematic diagram of a micropump according to the invention with cylindrical actuators.

FIG. 2 shows a schematic diagram of a micropump according to the invention with cylindrical actuators.

The micropump has five cylindrical actuators 15, which are arranged in a circle around a rotatable shaft 16. A flow channel 5 with a wall element 4 runs in a curved course, along a semicircular recess in a housing 17. The wall element 4, at least in the curved area, is made from an elastic material and can be compressed against the housing by the cylindrical actuators 1, such that its internal cross-sectional area can be reduced to virtually zero. Outside the wall element 4, on five portions of the channel, there are sensor arrangements 18, which are connected to an evaluation unit 10 via signal leads 9. Two cylindrical actuators 15 located next to each other isolate a volume segment 14 when both simultaneously close the flow channel 5 by the exertion of a force on the wall elements. On rotation of the rotating shaft 18, the cylindrical actuators 15 rotate around the shaft 16, thereby moving along the curved flow channel 5, with the result that the volume segments 14 isolated between two cylindrical actuators 15 are transported further in the flow channel 5. The pump action of the rotary pump is based on this principle. The sensor arrangements detect the quantity of liquid medium in a channel portion adjacent to them. With the rotation of the shaft 16 and the resulting movement of the cylindrical actuators 15, the quantity of liquid medium detected next to each of the sensor arrangements 18 periodically rises and falls in turn. In the event of a pump malfunction or a blockage, the pump produces deviant signals which are detected.

Figure 3:
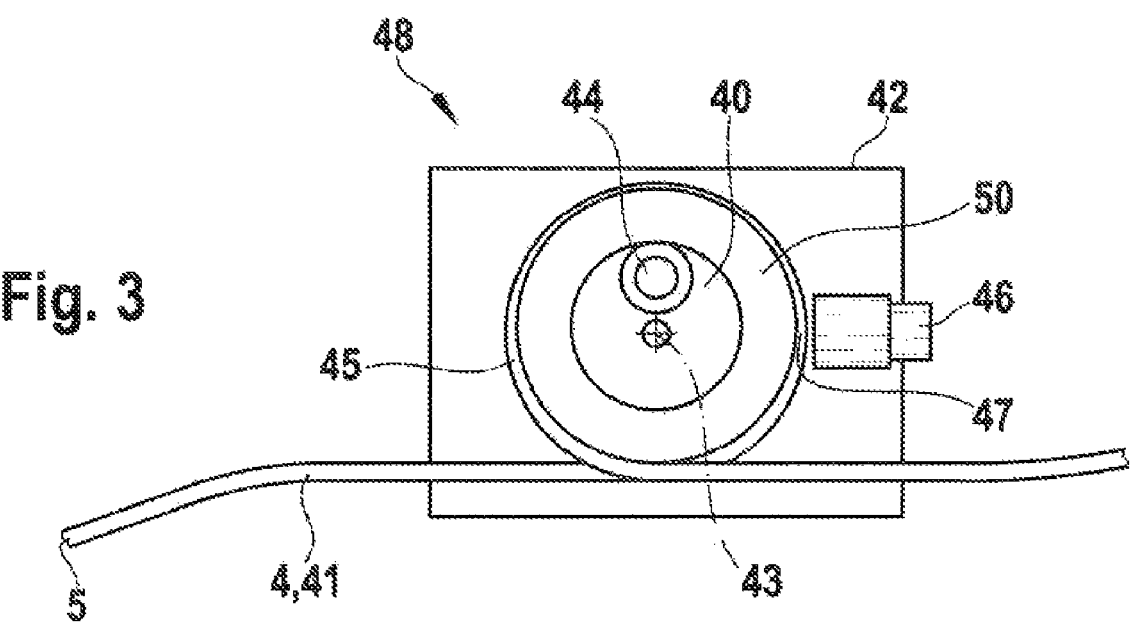
FIG. 3 shows a schematic diagram of a micropump according to the invention with a disc-shaped actuator.

FIG. 3 shows a schematic diagram of a micropump according to the invention with a disc-shaped actuator.

In this embodiment of the invention, a rotating first disc 40 is used as the actuator. A tube 41 is used as the wall element 4 which contains the flow channel 5. In the area adjacent to the first disc 40, within a housing 42, there is a second disc 50, adjacent to which is the flow channel 5 running in a near-circular course. The disc 40 rotates around the eccentric axis 43 to pump liquid medium. On the first disc 40 there is a roller 44, which on rotation of the first disc 40 about the axis 43 is pressed, in a circular path, against a second disc 50, which is pressed, in a circular path, against the wall element 45—which has a circular course—of the flow channel 5, whereby the cross-sectional area of the elastic wall element 45 with a circular course is reduced in a circular path, thereby pumping the liquid medium along. To drive the first disc 40, the housing 42 preferably contains a micromotor with standard gearing or a micromotor with a spindle (not shown). Outside the wall element 45, on a channel portion 47, the housing 42 also has a sensor arrangement 46, which can detect a quantity of the liquid medium in the channel portion 47. By means of the mechanical principle of the eccentric, a high degree of micropump reliability is achieved. Free, uncontrolled flow of the liquid medium is not possible. Thanks to the first disc 40 that moves around the eccentric axis 43 and to the resulting continuous pumping, the pumping is virtually independent of the (rotational) position of the first disc 40. In this eccentric pump 48, therefore, the monitoring by a sensor arrangement 46 leads to good quality assurance of pump function. Monitoring with several sensor arrangements is also possible, however. The eccentric pump 48 (e.g. with spindle drive) can be made very small, allowing it to be readily integrated into a housing, for example with an infusion needle arrangement 37 of a device for metered administration of a liquid drug, without any appreciable adverse effect on the comfort of the infusion needle arrangement 37 for the patient wearing it and with a simultaneous increase in overall reliability.

Figure 4:
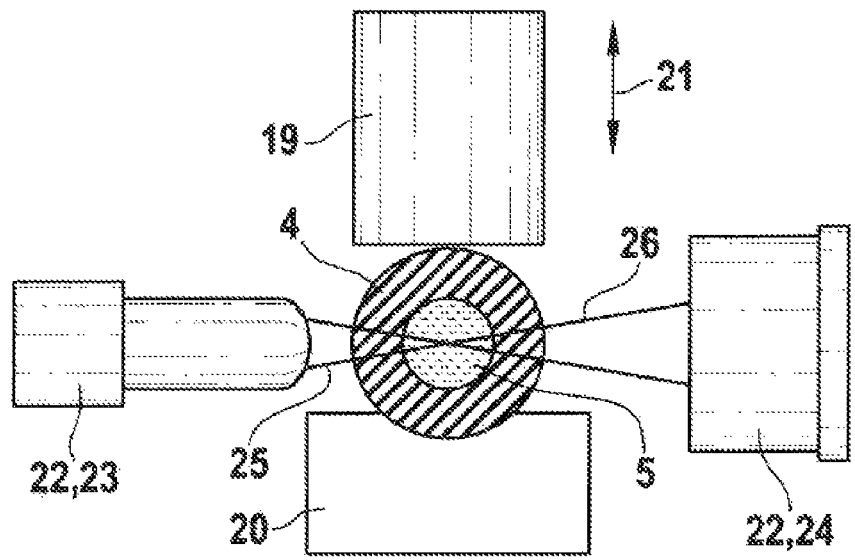
FIG. 4 shows a schematic diagram of the measurement principle of a first sensor arrangement for measuring the absorption of electromagnetic radiation in a micropump according to the invention.

FIG. 4 shows a schematic diagram of the measurement principle of a first sensor arrangement for measuring the absorption or fluorescence of electromagnetic radiation in a micropump according to the invention.

On the wall element 4 of a flow channel 5 there is an actuator 19 (for example a pin or an eccentric) and, opposite it, a block 20. The actuator 19 can be moved in the indicated direction of movement 21 and can thereby exert a force on the wall element 4 to alter the cross-sectional area of the flow channel 5. A sensor arrangement 22 comprises an electromagnetic radiation-emitting element 23 (for example an LED) and an electromagnetic radiation-detecting element 24 (for example a photodiode or the end of a light guide leading to a photodiode) sited next to the wall element 4, opposite, if necessary, the detecting element 24 contains a filter element (not shown), e.g. for fluorescence measurements or to lessen natural background radiation. The emitting element 23 is directed at the wall element 4, such that the emitted electromagnetic radiation 25 passes through the wall element 4 on one side, the flow channel 5, and the wall element 4 on the other side. The emitted electromagnetic radiation 25 is absorbed or generates fluorescence in the flow channels according to the quantity of liquid medium contained therein. The remaining unabsorbed, or the fluorescent fraction of the radiation emerges from the wall element 4 (transmitted electromagnetic radiation 26) and can be detected by the detecting element 24 and evaluated by an evaluation unit.

Figure 5:
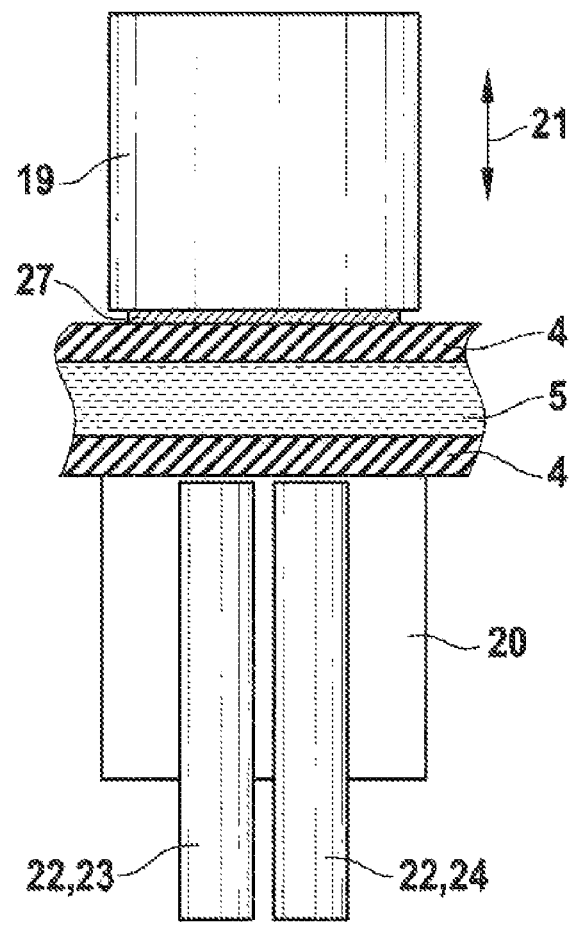
FIG. 5 shows a schematic diagram of a second sensor arrangement for measuring the absorption of electromagnetic radiation or the reflexion of ultrasound in a micropump according to the invention.

FIG. 5 shows a schematic diagram of a second sensor arrangement for measuring the absorption or fluorescence of electromagnetic radiation or the reflexion of ultrasound in a micropump according to the invention.

On the wall element 4 of a flow channel 5 there is an actuator 19 and, opposite it, a block 20. The actuator 19 (for example a pin, a roller, or an eccentric) can be moved in the indicated direction of movement 21 and can thereby exert a force on the wall element 4 to alter the cross-sectional area of the flow channel 5.

In a first embodiment, a sensor arrangement 22 comprises an electromagnetic radiation-emitting element 23 (for example an LED) and an electromagnetic radiation-detecting element 24 (for example a photodiode or a fibre-optic light guide, with a filter, if necessary) sited next to it on the wall element 4. The wall element 4 has a wall area 27, which is (at least partially) reflective (for example a light-reflecting layer). The electromagnetic radiation (not shown) emitted by the emitting element 23 passes through the wall element 4 and the flow channel 5 and hits the reflective wall area 27, from where some of the radiation is reflected towards the detecting element 24. The electromagnetic radiation is absorbed or generates fluorescence in the flow channel 5 according to the quantity of liquid medium contained therein. The remaining, unabsorbed, or the fluorescent, fraction of the radiation emerges from the wall element 4 and can be detected by the detecting element 24 and evaluated by an evaluation unit.

In a second embodiment, the sensor arrangement 22 comprises an ultrasound emitter 23 (based on a piezoelectric element for example) and an ultrasound receiver 24 sited next to it on the wall element 4. The wall element 4, at least in an area adjacent to the channel portion shown, contains a material with a certain acoustic impedance, which is chosen with regard to the acoustic impedance of the liquid medium. The ultrasound emitted by the ultrasound emitter 23 passes through the wall element 4 and the flow channel 5, and is reflected towards the ultrasound receiver 24 as a function of the acoustic impedance mismatch between the material contained in the flow channel 5 and the wall element material. The reflected fraction of the ultrasound emerges from the wall element 4 and can be detected by the ultrasound receiver 24 and evaluated by an evaluation unit to determine the quantity of liquid medium in the portion of the channel.

Figure 6:
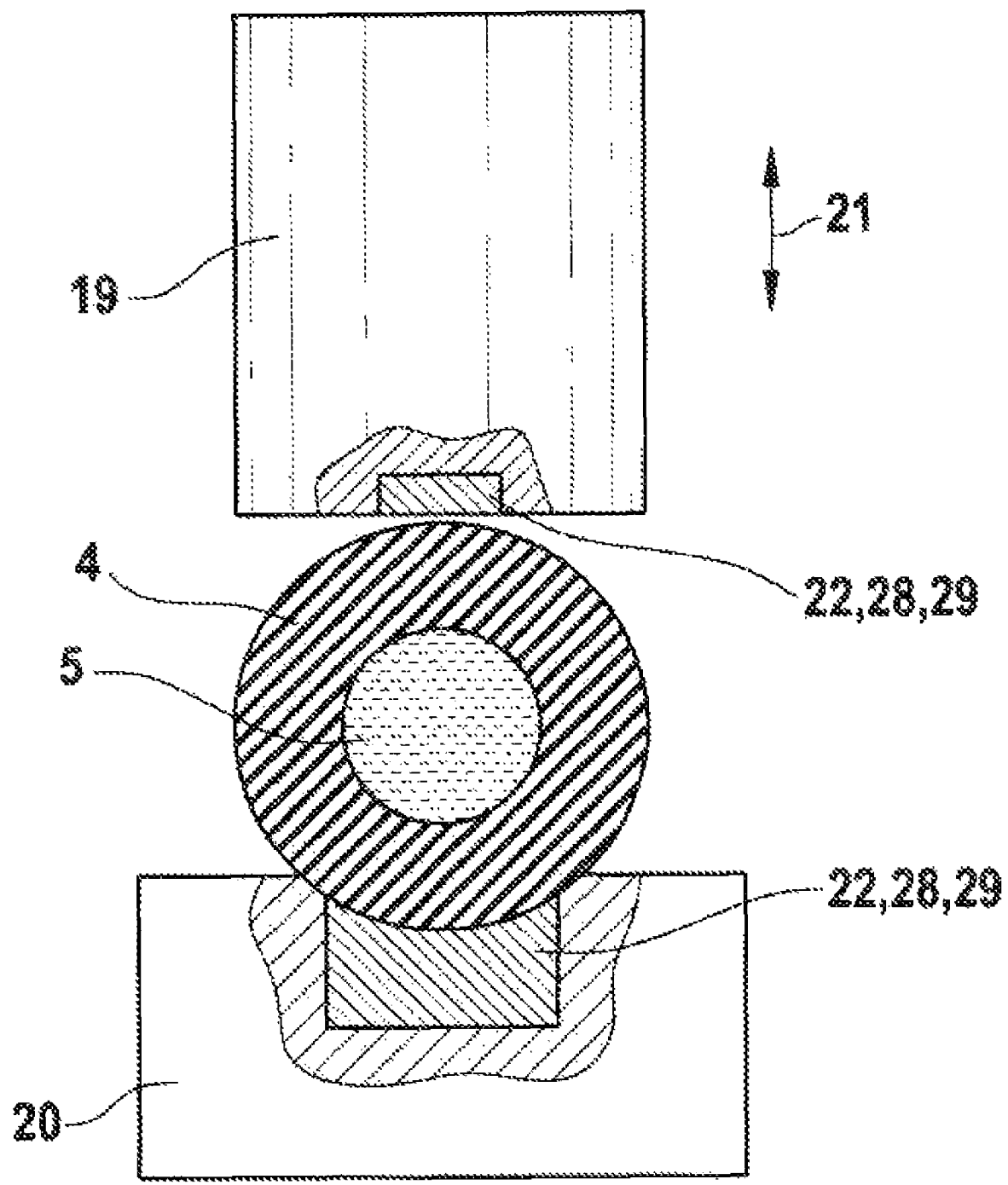
FIG. 6 shows a schematic diagram of a sensor arrangement for capacitance measurement or ultrasound measurement in a micropump according to the invention.

FIG. 6 shows a schematic diagram of a sensor arrangement for capacitance measurement or ultrasound measurement in a micropump according to the invention.

On the wall element 4 of a flow channel 5 there is an actuator 19 and, opposite it, a block 20. The actuator 19 can be moved in the indicated direction of movement 21 and can thereby exert a force on the wall element 4 to alter the cross-sectional area of the flow channel 5.

In a first embodiment, a sensor arrangement 22 comprises a capacitor 28 which contains capacitor plates 29 arranged on two sides of a portion of the flow channel 5, on the outside of the wall element 4. The capacitance of the capacitor 28 depends, among other things, on the quantity of liquid medium contained in the flow channel 5 between the capacitor plates 29. A measuring arrangement (not shown) measures the capacitance of the capacitor 28 to determine this quantity.

In a second embodiment, a sensor arrangement 22 comprises an ultrasound emitter 29 and an ultrasound receiver 29 which are arranged on two opposite sides of a portion of the flow channel 5, on the outside of the wall element 4. The transmitted fraction of the ultrasound transmitted from the ultrasound emitter 29 to the ultrasound receiver 29 through the flow channel 5 depends, among other things, on the quantity of liquid medium contained in the flow channel 5 between the ultrasound emitter 29 and the ultrasound receiver 29.

Figure 7:
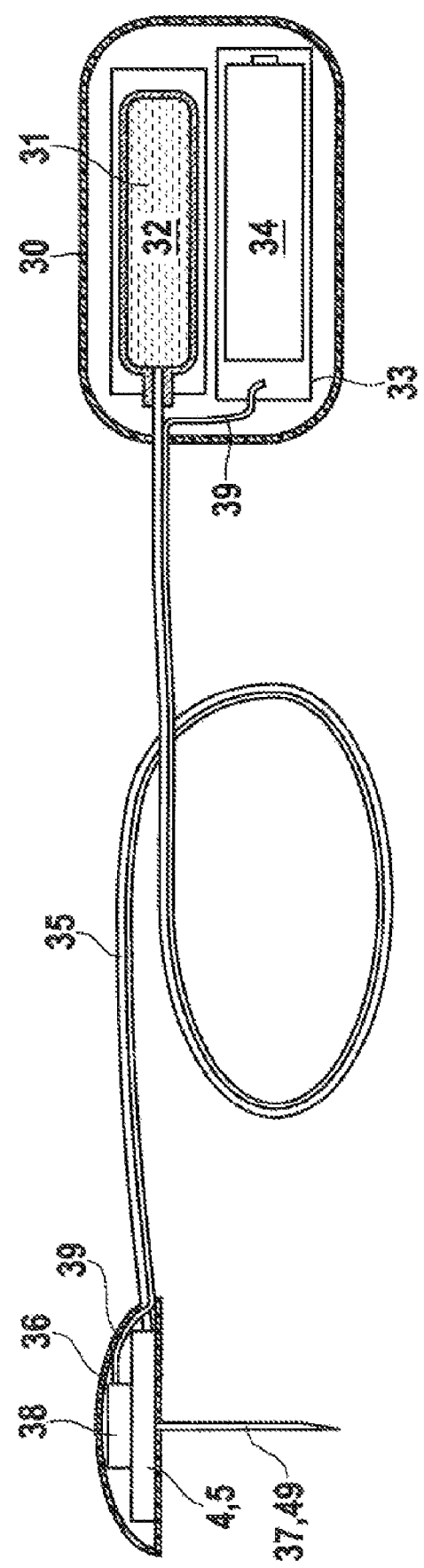
FIG. 7 shows a device according to the invention for metered administration of a liquid drug.

FIG. 7 shows a schematic diagram of a device according to the invention for metered administration of a liquid drug.

The device comprises a reservoir 31 which is held in a first housing 30 and which contains a liquid drug 32. It is, for example, an insulin container formed as a blister pack that folds up on emptying. In the first housing 30 there is also a control unit 33 with a battery 34. A user can send requirements to the control unit 33 via a manual operating element (not shown) or wholly or partly via a remote operating unit (not shown), for example. A connecting tube 35 is connected to the reservoir 31. The connecting tube 35 transports liquid drug 32 from the reservoir 31 to a second housing 36. Running along the connecting tube 35 there are also leads 39 to supply electricity and carry signals, these leads being connected to the control unit 33. In the second housing 36 there is an infusion needle arrangement 37, which is connected, via a flow channel 5 in a wall element 4, to the connecting tube 35 and the reservoir 31. The infusion needle arrangement 37 contains an infusion needle 49, which can, if necessary, "float" in the second housing 38 so that movements on the part of the patient and the resulting relative movements of the infusion needle 49 and housing 36 do not cause pain. In the second housing 36 there is also a micropump 38 according to the invention, which acts on the wall element 4 of the flow channel to pump the liquid drug 32. The micropump 38 is supplied with power and control signals via the leads 39 and sends measurement signals, of the sensor arrangements (not shown) contained in the micropump 38 to the control unit 33. The wall element 4 of the flow channel 5 is preferably detachably mounted in or on the micropump allowing the micropump to be removed from the second housing 36 without the flow channels, and allowing the rest of the device according to the invention to be disposed of. The micropump can be reused, for example by clipping a new wall element 4 of a flow channel 5 onto/into the micropump to obtain a new device according to the invention for metered administration of the liquid drug 32.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A micropump for peristaltic pumping of a liquid medium, the micropump comprising:
   at least one flow channel with a wall element, the flow channel having a cross-sectional area which, at least in subportions of the flow channel, can be altered by the exertion of a force on the wall element of the flow channel;
   actuators arranged in such a manner that they are able to exert the force on the wall element of the flow channel in at least two subportions of the channel to reduce the cross-sectional area in those subportions of the channel so that no liquid medium is detected in those subportions with reduced cross-sectional area;
   at least one sensor arrangement for detecting a quantity of liquid medium in the portion of the channel between the at least two subportions of the channel with reduced cross-sectional area and for calculating a volume of the liquid medium in the portion of the channel, the sensor arrangement being located outside the flow channel; and at least two further sensor arrangements for detecting the quantity of the liquid medium in the at least two subportions of the channel with reduced cross-sectional area, the at least two further sensor arrangements being located outside the flow channel.

2. The micropump according to claim 1, wherein the actuators comprise at least two actuators which are arranged in such a way that they are able to exert the force on the wall element of the flow channel in at least two portions of the channel, thereby temporarily closing the relevant portion of the channel and allowing a volume segment to be isolated in the flow channel, such that the sensor arrangement lying outside the flow channel can detect the quantity of liquid medium in the volume segment.

3. The micropump according to claim 1, further comprising at least three pin-shaped actuators which are arranged next to each other outside the flow channel and which comprise at least two valve pins and at least one pump pin.

4. The micropump according to claim 1, further comprising:
  a reservoir of the liquid medium, comprising a liquid drug, and
  an infusion needle arrangement wherein the reservoir being connected to the infusion needle arrangement by means of the flow channel.

* * * * *